United States Patent [19]

Kaye et al.

[11] 3,956,357
[45] May 11, 1976

[54] MANUFACTURE OF 2-CYANO-PROPIONATE ESTERS

[75] Inventors: Albert Edward Kaye; Alan Cyril Tucker; Ronald James Hurlock, all of Manchester, England

[73] Assignee: Imperial Chemical Industries Limited, London, England

[22] Filed: Mar. 13, 1975

[21] Appl. No.: 557,902

[30] Foreign Application Priority Data
Apr. 26, 1974 United Kingdom............ 18372/74

[52] U.S. Cl............................. 260/465.4; 260/464
[51] Int. Cl.² ..................................... C07C 120/00
[58] Field of Search ............................. 260/465.4

[56] References Cited
UNITED STATES PATENTS 3,173,939  3/1965  Johnson .......................... 260/465.4
3,350,439  10/1967 Feldman et al. ......... 260/465.8 R X

OTHER PUBLICATIONS

Migrdichian; The Chemistry of Organic Cyanogen Compounds: 1947; pp. 319 and 323; Reinhold Pub. Corp.

House; Modern Synthetic Reactions; 2nd ed., 1972; pp. 646–647; Benjamin, Inc.

Alexander, et al; J.A.C.S.; 66; pp. 886–888.

*Primary Examiner*—Joseph P. Brust
*Attorney, Agent, or Firm*—Cushman, Darby & Cushman

[57] ABSTRACT

A process for the manufacture of 2-cyano-propionate esters which comprises hydrogenating in the presence of an hydrogenating catalyst a mixture of a cyanoacetic ester, formaldehyde and a condensation catalyst. Typically ethyl cyano-acetate is treated with formalin or paraform and hydrogen in the presence of palladium on carbon and zinc acetate. Preferably an antioxidant or polymerisation inhibitor is also included in the reaction mixture which also usually includes solvents such as glacial acetic acid or toluene.

10 Claims, No Drawings

MANUFACTURE OF 2 CYANO PROPIONATE ESTERS

This invention relates to a process for the manufacture of 2 cyano-propionate esters.

2-cyanopropionate esters are of value as intermediates for the manufacture of medicinals.

According to the invention there is provided a process for the manufacture of 2-cyano-propionate esters which comprises hydrogenating in the presence of an hydrogenation catalyst a mixture of a cyanoacetic ester, formaldehyde and a condensation catalyst.

As hydrogenation catalysts there may be mentioned any conventional hydrogenation catalyst which is active at the moderate temperatures suitable for the process of the invention. Suitable catalysts include palladium, platinum, rhodium, cobalt or ruthenium supported on silica, alumina or carbon and Raney nickel. In the case of 3% palladium supported on carbon amounts of from 1 to 10% of the weight of formaldehyde and cyanoacetic ester are usually satisfactory.

As cyanoacetic esters there may be mentioned cyclo alkyl such as cyclo hexyl, substituted alkyl such as 2 hydroxy ethyl, 2 cyano ethyl and especially lower alkyl particularly ethyl esters.

Formaldehyde can be used in the form of a gas, an aqueous solution such as formalin, or as any of its derivatives which decomposes to yield formaldehyde under the conditions of the process, for example polymers such as paraform or derivatives such as diethyl formal.

As condensation catalysts there may be mentioned any catalyst conventionally used to bring about reaction of aldehydes with active methylene groups, for example basic catalysts such as ammonia or amines, e.g. piperidine or diethylamine optionally in the form of salts with organic acids such as acetic, butyric or oxalic acid, basic ion-exchange resins, and acid catalysts, such as acetic acid and metallic salts including catalysts of the Friedel-Crafts type, such as zinc chloride, zinc acetate, magnesium chloride, barium chloride, ferric chloride, aluminium chloride.

The amount of catalyst used depends upon the type of catalyst. Basic catalysts are conveniently used in amount between 0.5 and 10% (calculated as free base), or preferably between 2 and 6%, of the weights of formaldehyde and cyano-acetic ester combined. Acid catalysts are peferably used in somewhat greater proportions and it is often convenient to use a solution of a salt such as zinc chloride in acetic acid.

The process may be carried out conveniently at any temperature between 15° and about 80°C. Higher temperatures may be used but tend to cause side reactions. It is frequently preferable to commence the reaction at a low temperature, for example 20° to 30°C, and then complete the hydrogenation at a temperature near 70°C.

The process requires equimolecular proportions of formaldehyde and cyano acetic ester but it is often preferable to use a slight, for example up to 5% excess of formaldehyde to ensure complete conversion of the cyano acetic ester. Proportions differing from these may be used with some loss in efficiency.

The process may be carried out by mixing the reactants and catalysts and simultaneously adding the hydrogen, but it is usually preferable to introduce the hydrogen before the formaldehyde. It is frequently advantageous to control the reaction by regulated addition of either the reactants or the condensation catalyst as the reaction proceeds. The hydrogen may be passed through the reaction mixture or the reaction mixture may be stirred under an atmosphere of hydrogen, preferably at superatmospheric pressure, further hydrogen being if desired added as necessary to maintain the pressure.

If desired stabilisers such as antioxidants or polymerisation inhibitors may be added to the reactants to reduce undesirable side-reactions. Suitable stabilisers include anthraquinone hydroquinones, and alkyl phenols such as 2:4 dimethyl-6-t-butylphenol. These stabilisers are usually added in amounts between 0.1 and 5.0% preferably between 0.2 and 2.0% of the weights of formaldehyde and cyanoacetic ester combined.

If desired the process may be carried out in a solvent such as ethanol or acetic acid, a solvent of the latter type acting also as a condensation catalyst. Water may be present, for example when formaldehyde is used as formalin.

If desired the reaction may be carried out in the presence of an inert, substantially water immiscible solvent such as hexane, Toluene. This water immiscible solvent may be used alone or in conjunction with water or a water miscible solvent.

The product may be isolated for example by removing the insoluble hydrogenation catalyst by filtration and distillation of the filtrate under reduced pressure.

The invention is illustrated but not limited by the following Examples in which all parts and percentages are by weight unless otherwise stated.

EXAMPLE 1

3 Parts of paraformaldehyde, 20 parts of glacial acetic acid, 0.6 parts of zinc acetate, 1.5 parts of a 3% palladium on carbon catalyst, 0.5 parts of anthraquinone and 11.3 parts of ethyl cyanoacetate are stirred together under an atmosphere of hydrogen at 40°–45°C. After 19 hours uptake of hydrogen ceases. The mixture is filtered, diluted with 40 parts of water and extracted with three successive 20 parts of ether. Distillation of the ether extract under reduced pressure gives 1.8 parts of ethyl 2-cyano propionate of boiling point 99–102°C/13 mm. of mercury.

EXAMPLE 2

22.6 Parts of ethyl cyanoacetate, 1.5 parts of a 3% palladium on carbon catalyst, 2 parts of piperidine, 3 parts of glacial acetic acid and 0.5 parts of a stabiliser commercially available as "Topanol A", ("Topanol" is a registered Trade Mark) are stirred at 20–25°C under a hydrogen atmosphere. 10.8 Parts of formalin (36% formaldehyde) are added over 37¼ hours at a rate proportional to the hydrogen uptake. After a further 6¾ hours hydrogen uptake is complete. The reaction mixture is filtered and extracted with three successive 20 parts of chloroform. Distillation under reduced pressure gives 9 parts of a distillate boiling at 86°–152°C/11 mm. of mercury containing 7.6 parts of ethyl 2-cyano propionate.

EXAMPLE 3

Using the procedure of Example 2 with 0.5 parts of m-dinitrobenzene in place of the Topanol A and 11.8 parts of formalin added over 45 hours, 9.7 parts of ethyl 2-cyano propionate were obtained.

EXAMPLE 4

22.6 Parts of ethyl cyanoacetate, 1.5 parts of a 3% palladium on charcoal catalyst and 10 parts of water are mixed under a nitrogen atmosphere and heated to 60°C. The nirogen is displaced by hydrogen and 20 parts of a solution made from 20 parts of formalin (36%), 1.7 parts of piperidine, 1.5 parts of acetic acid and water to give a total of 30 parts, are added over 5½ hours at a rate equivalent to the hydrogen uptake. The reaction mixture is cooled, filtered and extracted by three successive 20 parts of ether. Distillation under reduced pressure of the ether extract gave 9.8 parts of ethyl 2-cyano propionate boiling point 80–95°C/9 mm. of mercury.

EXAMPLE 5

11.3 Parts of ethyl cyano acetate, 200 parts of toluene, 0.25 parts of hydroquinone, 1.5 parts of a 3% palladium on charcoal catalyst and 0.25 parts of piperidine are stirred under an atmosphere of hydrogen. 8.6 Parts of a mixture of 10 parts of formalin (36%), and 0.85 Parts of piperidine, 0.75 parts of glacial acetic acid and water to give a total of 15 parts is added in 0.2 part portions over 11¾ hours. The temperature of the reaction mixture is raised to 60° over the first hour of addition and maintained at that level during the remainder of the addition. The reaction mixture is filtered and the toluene layer separated. Distillation of the toluene layer gives 5.4 parts of ethyl 2-cyanopropionate of boiling point 86–100°C/14 mm. of mercury.

EXAMPLE 6

11.3 Parts of ethyl cyanoacetate, 200 parts of ethanol, 0.25 parts of a stabiliser commercially available as "Topanol" A ("Topanol" is a registered trade mark) 0.25 parts of piperidine and 1.5 parts of a 3% palladium on charcoal catalyst are stirred under an atmosphere of hydrogen at 30°C. 12 Parts of a mixture of formalin piperidine, water and acetic acid similar to that described in Example 5 are added over 10¾ hours. The temperature is raised to 40°C over the first 4 hours of addition and maintained at that level during the remainder of the addition. The reaction mixture is filtered and the ethanol removed by distillation under reduced pressure. 100 Parts of water and 100 parts of toluene are added to the residue. The toluene layer is separated, washed with two 50 parts of 5% sodium bisulphite solution and once with water. Distillation of the toluene solution under reduced pressure yields 4 parts of ethyl 2-cyano propionate, boiling point 80°–110°C/16–19 mm. of mercury.

EXAMPLE 7

22.6 Parts of ethyl cyanoacetate, 0.5 parts formalin, 0.2 parts piperidine, 0.4 parts of glacial acetic acid 1.5 parts of a 3% palladium on charcoal catalyst and 200 parts of water are mixed under an atmosphere of hydrogen. 10 Parts of formalin are added over 30 hours at a temperature of 30°C for the first 11 hours and 40°C for the remainder. The reaction mixture is cooled, 50 parts of ether added and filtered. After separation the aqueous portion of the filtrate is extracted with a further 20 parts of ether. Distillation of the combined ether solutions under reduced pressure gave 9.9 parts of a distillate boiling at 84–148°C at 10 mm. of mercury which contained 6.9 parts of ethyl 2-cyano propionate.

EXAMPLE 8

Following the procedure of Example 5 omitting the 0.25 parts of piperidine and 0.025 parts of hydroquinone and adding 9.6 parts of the formalin, piperidine and acetic acid solution in place of the 8.6 parts of Example 5 over 15¼ hours gave 6.8 parts of ethyl 2-cyanopropionate of boiling point 82–90°C/8 mm. of mercury.

EXAMPLE 9

904 Parts of ethyl cyano acetate, 10 parts of hydroquinone, 4.3 parts of piperidine, 45 parts of 3% palladium on charcoal catalyst and 6,500 parts of toluene are mixed at 60°C under an atmosphere of hydrogen maintained at 30 p.s.i.g., 1,000 Parts of a solution made from 1,000 parts of formalin (36%), 75 parts of acetic acid, 86 parts of piperidine and water to give a total of 1,500 parts are added at a uniform rate over 3 hours the temperature being maintained at 60°–65°C. The reaction mixture is cooled, filtered and the toluene layer separated. Distillation under reduced pressure of the toluene layer yields 374.7 parts of ethyl 2-cyanopropionate boiling point 91°–118°C/20 mm. of mercury.

EXAMPLE 10

Using the procedure of Example 9 with 3,616 parts of ethyl cyanoacetate, 10 parts of hydroquinone, 4.3 parts of piperidine, 45 parts of a 3% palladium on charcoal catalyst and 6,500 parts of toluene, treated over 4 hours with 4,000 parts of a solution of 3,000 parts of formalin (36%), 225 parts of glacial acetic acid, 258 parts of piperidine and water to give a total of 4,500 parts, gave 1,488 parts of crude ethyl 2 cyanopropionate which on redistillation yielded 1198.5 parts of a purified product of boiling point 83°–85°C/12–13 mm. of mercury.

EXAMPLE 11

Using the procedure of Example 9, 1,808 parts of ethyl cyanoacetate, 10 parts of hydroquinone, 4.3 parts of piperidine, 45 parts of a 3% palladium on charcoal catalyst and 6,500 parts of toluene were treated over 10 hours with 2,000 parts of a solution of 2,000 parts of formalin, 150 parts of glacial acetic acid, 172 parts of piperidine and water to give a total of 3,000 parts, to yield 1330.5 parts of crude ethyl 2-cyanopropionate which redistilled to yield 1,239 parts of pure product boiling at 83°–84°C/13 mm.

We claim:

1. A process for the manufacture of a lower alkyl 2-cyano-propionate ester which comprises hydrogenating at a temperature of 15° to 80°C and in the presence of a hydrogenation catalyst, a reaction mixture of a cyano-acetic lower alkyl ester, formaldehyde and a condensation catalyst suitable for reacting formaldehyde with active methylene groups, and recovering the lower alkyl 2-cyanopropionate thus produced, hydrogen being introduced to the reaction mixture before the formaldehyde is added thereto and the hydrogenation catalyst being selected from the group consisting of palladium, platinum, rhodium, cobalt, ruthenium and Raney nickel.

2. A process as claimed in claim 1 wherein the catalyst is palladium.

3. A process as claimed in claim 1 in which the formaldehyde is added in the form of a derivative which yields formaldehyde under the reaction conditions.

4. A process as claimed in claim 1 wherein the condensation catalyst is a basic material.

5. A process as claimed in claim 4 in which the condensation catalyst is ammonia or an amine or an organic acid salt thereof or a basic ion exchange resin.

6. A process as claimed in claim 1 wherein the condensation catalyst is an acidic material.

7. A process as claimed in claim 5 in which the condensation catalyst is an organic acid or a metallic salt.

8. A process as claimed in claim 1 wherein the condensation catalyst is a Friedel-Crafts type catalyst.

9. A process as claimed in claim 1 when carried out in the presence of an antioxidant or polymerisation inhibitor.

10. A process as claimed in claim 1 wherein the condensation catalyst is selected from the group consisting of ammonia, piperidine, diethylamine, salts of piperidine or diethylamine with acetic acid, butyric acid or oxalic acid, zinc chloride, zinc acetate, magnesium chloride, barium chloride, ferric chloride, aluminum chloride, or acetic acid.

* * * * *